(12) United States Patent
Böttcher et al.

(10) Patent No.: US 6,583,286 B1
(45) Date of Patent: Jun. 24, 2003

(54) METHOD FOR HYDROGENATING UNSATURATED HETEROCYCLIC COMPOUNDS

(75) Inventors: Arnd Böttcher, Frankenthal (DE); Melanie Brunner, Schifferstadt (DE); Jochem Henkelmann, Mannheim (DE); Heinz Rütter, Hochdorf-Assenheim (DE); Boris Breitscheidel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/743,895

(22) PCT Filed: Jul. 20, 1999

(86) PCT No.: PCT/EP99/05178

§ 371 (c)(1),
(2), (4) Date: Jan. 17, 2001

(87) PCT Pub. No.: WO00/05184

PCT Pub. Date: Feb. 3, 2000

(30) Foreign Application Priority Data

Jul. 21, 1998 (DE) .......................................... 198 32 810

(51) Int. Cl.$^7$ .............................................. C07P 211/02
(52) U.S. Cl. ...................................................... 546/185
(58) Field of Search ......................................... 546/185

(56) References Cited

PUBLICATIONS

Occelli et al, Chem. Abs. vol. 130 No. 314069, "Physico-chemical properties of some metal supports for hydrotreating catalysts preparation", 1999.*

* cited by examiner

Primary Examiner—Ceila Chang
Assistant Examiner—Raymond Covington
(74) Attorney, Agent, or Firm—Keil & Weinkauf

(57) ABSTRACT

A process for hydrogenating an unsaturated heterocyclic compound or a mixture of two or more thereof by contacting the unsaturated heterocyclic compounder the mixture of two or more thereof with a hydrogen-containing gas in the presence of a catalyst comprising as active metal at least one metal from transition group VIII of the Periodic Table, applied to a support, wherein the support has macropores.

16 Claims, No Drawings

METHOD FOR HYDROGENATING UNSATURATED HETEROCYCLIC COMPOUNDS

This application is a 371 of PCT/EP99/05178, Jul. 20, 1999.

The present invention relates to a process for hydrogenating unsaturated heterocyclic compounds by contacting one or more unsaturated heterocylic compounds, especially pyridine or its derivatives, with a hydrogen-containing gas in the presence of a macroporous catalyst.

DE-A 16 20 664 relates to a process for preparing piperidine and its alkyl homologs by catalytic hydrogenation of pyridine and its alkyl homologs at temperatures from 100 to 200° C. and pressures of up to 200 bar in the presence of nickel catalysts comprising at least 30% by weight of nickel on active $Al_2O_3$ or chromium oxide.

JP 52 148 083 describes the preparation of piperidine from pyridine at from 100 to 200° C. in the presence of hydrogenation catalysts comprising ruthenium. The catalysts described therein are pretreated with sulfur compounds, such as mercaptans, thiophenes and sulfolanes, for example, prior to hydrogenation. This pretreatment with sulfur compounds, however, is comparatively laborious and impacts negatively on the hydrogenation activity of the catalysts used.

Pyridine can also be hydrogenated to piperidine over a supported ruthenium catalyst whose support comprises carbon or $\gamma$-$Al_2O_3$ with approximately 5% of ruthenium at from 80 to 130° C. and from 20 to 120 bar, as is described in SU 255 940. According to the process described therein, however, high metal loadings of 5% by weight or more are required to achieve high hydrogenation activities.

According to U.S. Pat. No. 1,315,260, pyridines and their acid addition salts are converted to the corresponding piperidines and their salts in the presence of from 0.05 to 2% by weight of ruthenium, which can be present as the finely divided metal on a support or as the dioxide, at from 60 to 90 bar and from 70 to 100° C., preferably in an inert solvent. A disadvantage of this process is that an inert solvent must be used in order to obtain high selectivities.

Similarly, 2-alkylpiperidines can be prepared without using a solvent by employing a catalyst comprising from 0.1 to 10% by weight of ruthenium or $RuO_2$ on $Al_2O_3$ or activated carbon, as is described in DE-A 25 50 716. According to this document, the hydrogenation is conducted at pressures <50 bar and at a temperature of from 160 to 180° C. The selectivity of this process, however, is inadequate. A further disadvantage is that the use of this process is limited to alkyl-substituted pyridines; under the conditions indicated therein and using the catalyst described therein it is not possible to hydrogenate pyridine to piperidine.

It is an object of the present invention to provide an improved process for selectively hydrogenating unsaturated heterocyclic compounds, especially pyridine and/or its homologs, to piperidine and/or its homologs, achieving very high yields and virtually complete conversion.

It is also an object of the present invention to provide such a process in which only a minimal fraction of byproducts and decomposition products is obtained during the hydrogenation. In addition, it should be possible to conduct the process of the invention with an extremely high turnover number under conditions of high space velocities and long service lives for the catalyst, with the corresponding hydrogenation products being obtained in high yield and high purity.

We have found that these objects, and others, are achieved by the process provided by this specification.

The present invention accordingly provides a process for hydrogenating an unsaturated heterocyclic compound or a mixture of two or more thereof by contacting the unsaturated heterocyclic compound or the mixture of two or more thereof with a hydrogen-containing gas in the presence of a catalyst whose active metal comprises at least one metal from transition group VIII of the Periodic Table, applied to a support, wherein said support has macropores.

In one preferred embodiment the present invention provides a process as defined above wherein the catalyst comprises as active metal at least one metal from transition group VIII of the Periodic Table alone or together with at least one metal from transition group I or VII if the Periodic Table, applied to a support, said support having an average pore diameter of at least 50 nm and a BET surface area of not more than 30 $m^2$/g and the amount of said active metal being from 0.01 to 30% by weight based on the overall weight of the catalyst (catalyst 1).

The invention also provides such a process wherein the catalyst comprises as active metal at least one metal from transition group VIII of the Periodic Table alone or together with at least one metal from transition group I or VII of the Periodic Table in an amount of from 0.01 to 30% by weight, based on the overall weight of the catalyst, applied to a support, from 10 to 50% of the pore volume of the support being formed by macropores having a pore diameter in the range from 50 nm to 10,000 nm and from 50 to 90% of the pore volume of the support being formed by mesopores having a pore diameter in the range from 2 to 50 nm, the sum of the pore volumes adding to 100% (catalyst 2).

In a further preferred embodiment the present invention provides a process as defined above wherein the catalyst (catalyst 3) comprises as active metal at least one metal from transition group VIII of the Periodic Table alone or together with at least one metal from transition group I or VII of the Periodic Table in an amount of from 0.01 to 30% by weight, based on the overall weight of the catalyst, applied to a support, said-support having an average pore diameter of at least 0.1 $\mu$m and a BET surface area of not more than 15 $m^2$/g.

As active metals it is preferred to employ platinum, rhodium, palladium, cobalt, nickel or ruthenium or a mixture of two or more thereof, ruthenium in particular being used as active metal. Among the metals which can likewise be used from transition group I or VII, or else from transition groups I and VII, of the Periodic Table, all of which can likewise be used in principle, preference is given to employing copper and/or rhenium.

The terms "macropores" and "mesopores" are used in the context of the present invention as they are defined in Pure Appl. Chem., 45 (1976) 79, namely as pores whose diameter is above 50 nm (macropores) or whose diameter is between 2 nm and 50 nm (mesopores).

The active metal content is generally from approximately 0.01 to approximately 30% by weight, preferably from approximately 0.01 to approximately 5% by weight, and in particular, from approximately 0.1 to approximately 5% by weight, based in each case on the overall weight of the catalyst used. For catalysts 1 to 3 employed with preference, which are described below, the active metal contents used with preference are stated again individually in the context of the discussion of these catalysts.

The term "heterocyclic unsaturated compound" used according to the invention embraces all cyclic compounds having at least one heteroatom, i.e., all compounds having at least one nitrogen, phosphorus, oxygen or sulfur atom, which are also unsaturated. In this context the term "unsaturated" embraces both cyclic compounds having isolated or conjugated double bonds and aromatic compounds. Owing to the selective hydrogenation capacity of the catalysts used herein, the compounds to be hydrogenated may also carry functional groups which can in principle be hydrogenated or reduced, respectively, such as —CHO, —CH$_2$OH, —COOH, —COOR (R=alkyl), —CH$_2$COOH, —CH$_2$COOR (R=alkyl), etc. It is of course also possible to hydrogenate compounds of the above type which are substituted by nonreducible groups, such as alkylpyridines, for example.

The compounds employed in each case are then reacted selectively to form the corresponding ring-hydrogenated compounds.

Particular mention may be made of the following compounds and classes of compounds: pyridines, pyrans, thiopyrans, picolines, pyrroles, furans, thiophenes, indoles, pyrazoles, imidazoles, azepines, thiazoles and pyrazines.

The following reactions in particular are conducted with the present process:

ring hydrogenation of pyrroles to the corresponding tetrahydropyrroles (pyrrolidines);

hydrogenation of quinoline to decahydroquinoline;

conversion of isoquinoline to decahydroisoquinoline;

conversion of indole to octahydroindole;

conversion of isoindole to octahydroisoindole;

conversion of acridine to tetradecahydroacridine;

conversion of pyridine to piperidine;

conversion of furan to tetrahydrofuran;

conversion of nicotinic acid, picolinic acid or isonicotinic acid to the corresponding ring-hydrogenated derivatives.

The parameters generally used for these reactions are described again briefly below in the section "the process regime".

In the text immediately below the catalysts 1 to 3 used with preference will be described in detail. They are described, by way of example, with reference to the use of ruthenium as an active metal. The indications below can also be transferred to the other active metals which can be used as defined herein.

Catalyst 1

The catalysts 1 used in accordance with the invention can be prepared industrially by applying at least one metal from transition group VIII of the Periodic Table with or without at least one metal from transition group I or VII of the Periodic Table to a suitable support.

The application can be made by impregnating the support in aqueous metal salt solutions, such as aqueous ruthenium salt solutions, by spraying corresponding metal salt solutions onto this support, or by other suitable techniques. Suitable metal salts of transition group I, VII or VIII of the Periodic Table are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts which in addition to the metal from transition group VIII of the Periodic Table comprise further metals applied as active metal to the support, the metal salts or metal salt solutions can be applied simultaneously or in succession.

The supports coated or impregnated with the metal salt solution are subsequently dried, preferably at temperatures from 100 to 150° C., and if desired are calcined at temperatures from 200 to 600° C., preferably from 350 to 450° C. In the case of separate impregnation, the catalyst is dried and, if desired, calcined following each impregnation step, as described above. In this case, the sequence in which the active components are applied by impregnation is freely selectable.

Subsequently, the coated and dried and, if desired, calcined supports are activated by treatment in a stream of gas containing free hydrogen at temperatures from approximately 30 to approximately 600° C., preferably from approximately 150 to approximately 450° C. The stream of gas consists preferably of from 50 to 100% by volume H$_2$ and from 0 to 50% by volume N$_2$.

The metal salt solution or solutions is or are applied to the support or supports in an amount such that the total active metal content, based in each case on the overall weight of the catalyst, is from approximately 0.01 to approximately 30% by weight, preferably from approximately 0.01 to approximately 5% by weight, more preferably from 0.01 to approximately 1% by weight and, with particular preference, from approximately 0.05 to approximately 1% by weight.

The metal surface area on the catalyst 1 is in total from approximately 0.01 to approximately 10 m$^2$/g, more preferably from approximately 0.05 to approximately 5 m$^2$/g and, in particular, from approximately 0.05 to approximately 3 m$^2$/g of the catalyst. The metal surface area is determined by means of the chemisorption techniques described by J. LeMaitre et al. in "*Characterization of Heterogenous Catalysts*", ed.

Francis Delanney, Marcel Dekker, New York 1984, pp. 310–324.

In the catalyst 1 used in accordance with the invention the ratio of the surface areas of the active metal/metals and of the catalyst support is preferably less than approximately 0.05, the lower limit being approximately 0.0005.

The support materials which can be used to reduce the catalysts used in accordance with the invention are those which are macroporous and have an average pore diameter of at least approximately 50 nm, preferably at least approximately 100 nm, in particular at least approximately 500 nm and whose BET surface area is not more than approximately 30 m$^2$/g, preferably not more than approximately 30 m$^2$/g, more preferably not more than approximately 10 m$^2$/g, in particular not more than approximately 5 m$^2$/g and, with further preference, not more than approximately 3 m$^2$/g. The average pore diameter of the support is preferably from approximately 100 nm to approximately 200 μm, more preferably from approximately 500 nm to approximately 50 μm. The surface area of the support is preferably from approximately 0.2 to approximately 15 m$^2$/g, more preferably from approximately 0.5 to approximately 10 m$^2$/g, in particular from approximately 0.5 to approximately 5 m$^2$/g and, with further preference, from approximately 0.5 to approximately 3 m$^2$/g.

The surface area of the support is determined in accordance with the BET technique by N$_2$ adsorption, in particular in accordance with DIN 66131. The average pore diameter and the pore size distribution are determined by Hg porosimetry, in particular in accordance with DIN 66133.

Preferably, the pore size distribution of the support can be approximately bimodal; the pore diameter distribution having maxima at approximately 600 nm and about 20 μm in the case of bimodal distribution constitutes a specific embodiment of the invention.

Preference is also given to a support having a surface area of 1.75 m$^2$/g and featuring this bimodal distribution of the pore diameter. The pore volume of this preferred support is preferably about 0.53 ml/g.

Examples of materials which can be used as macroporous supports are activated carbon, silicon carbide, alumina, silica, titanium dioxide, zirconium dioxide, magnesium oxide, zinc oxide or mixtures of two or more of these, with preference being given to the use of alumina and zirconium oxide.

Further details regarding catalyst 1 and its preparation can be found in DE-A 196 24 484.6, the relevant content of which is incorporated fully into the present specification by reference.

Catalyst 2

The catalysts 2 used in accordance with the invention comprise one or more metals from transition group VIII of the Periodic Table as active component(s) on a support as defined herein. Preference is given to using ruthenium, palladium and/or rhodium as active component(s).

The catalysts 2 used in accordance with the invention can be produced industrially by applying at least one active metal from transition group VIII of the Periodic Table, preferably ruthenium or palladium, with or without at least one metal from transition group I or VII of the Periodic Table, to an appropriate support. The application can be made by impregnating the support in aqueous metal salt solutions, such as ruthenium salt solutions or palladium salt solutions, by spraying corresponding metal salt solutions onto this support, or by other suitable techniques. Suitable metal salts for preparing the metal salt solutions are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts which comprise two or more active metals supplied to the support, the metal salts or metal salt solutions can be applied simultaneously or in succession.

The supports coated or impregnated with the metal salt solution are subsequently dried, preferably at temperatures from 100 to 150° C., and if desired are calcined at temperatures from 200 to 600° C., preferably from 350 to 450° C. Subsequently, the coated supports are activated by treatment in a stream of gas containing free hydrogen at temperatures from 30 to 600° C., preferably from 100 to 450° C. and, in particular, from 100 to 300° C. The stream of gas consists preferably of from 50 to 100% by volume $H_2$ and from 0 to 50% by volume $N_2$.

Where two or more active metals are applied to the support in succession, the support can be dried at temperatures from 100 to 150° C. following each application or impregnation and, if desired, can be calcined at temperatures from 200 to 600° C. In this case the sequence in which the metal salt solutions are applied, or applied by impregnation, is arbitrary.

The metal salt solution is applied to the support or supports in an amount such that the active metal content, based on the overall weight of the catalyst, is from 0.01 to 30% by weight, preferably from 0.01 to 10% by weight, more preferably from 0.01 to 5% by weight and, in particular, from 0.3 to 1% by weight.

The metal surface area on the catalyst is in total from approximately 0.01 to approximately 10 $m^2/g$, from approximately 0.05 to approximately 5 $m^2/g$ and, in particular, from approximately 0.05 to approximately 3 $m^2/g$ of the catalyst. The metal surface area was measured by the chemisorption technique as described in J. LeMaitre et al., in "*Characterization of Heterogenous Catalysts*", ed. Francis Delanney, Marcel Dekker, New York 1984, pp. 310–324.

In the catalyst 2 used in accordance with the invention the ratio of the surface areas of the active metal/metals and of the catalyst support is less than approximately 0.3, preferably less than approximately 0.1, and in particular, approximately 0.05 or less, the lower limit being approximately 0.0005.

The support materials which can be used to prepare the catalysts 2 used in accordance with the invention possess macropqrous and mesopores.

In this context, the supports which could be used in accordance with the invention have a pore distribution formed to the extent of from approximately 5 to approximately 50%, preferably from approximately 10 to approximately 45%, more preferably from approximately 10 to approximately 30% and, in particular, from approximately 15 to approximately 25% of the pore volume by macropores having pore diameters in the range from approximately 50 nm to approximately 10,000 nm, and to the extent of from approximately 50 to approximately 95%, preferably from approximately 55 to approximately 90%, more preferably from approximately 70 to approximately 90% and, in particular, from approximately 75 to approximately 95% of the pore volume by mesopores having a pore diameter of from approximately 2 to approximately 50 nm, the sum of the pore volumes adding to 100% in each case.

The overall pore volume of the supports used in accordance with the invention is from approximately 0.05 to 1.5 $cm^3/g$, preferably from 0.1 to 1.2 $cm^3/g$ and, in particular, from approximately 0.3 to 1.0 $cm^3/g$. The average pore diameter of the supports used in accordance with the invention is from approximately 5 to 20 nm, preferably from approximately 8 to approximately 15 nm and, in particular, from approximately 9 to approximately 12 nm.

The surface area of the support is preferably from approximately 50 to approximately 500 $m^2/g$, more preferably from approximately 200 to approximately 350 $m^2/g$ and, in particular, from approximately 250 to approximately 300 $m^2/g$ of the support.

The surface area of the support is determined in accordance with the BET technique by $N_2$ adsorption, in particular in accordance with DIN 66131. The average pore diameter and the pore size distribution are determined by Hg porosimetry in particular in accordance with DIN 66133.

Although it is possible in principle to employ any of the support materials known for catalyst preparation, i.e., those having the pore size distribution defined above, preference is given to employing activated carbon, silicon carbide, alumina, silica, titanium dioxide, zirconium dioxide, magnesium oxide, zinc oxide or mixtures thereof, with preference being given to alumina and zirconium oxide.

Further details regarding catalyst 2 and its preparation can be found in DE-A 196 24 485.4, the relevant content of which is incorporated fully into the present specification by reference.

Catalyst 3

The catalysts 3 used in accordance with the invention can be prepared industrially by applying at least one metal from transition group VIII of the Periodic Table with or without at least one metal from transition group I or VII of the Periodic Table to a suitable support. The application can be made by impregnating the support in aqueous metal salt solutions, such as ruthenium salt solutions, by spraying corresponding metal salt solutions onto this support, or by other suitable techniques. Suitable ruthenium salts for preparing the ruthenium salt solutions and suitable metal salts of transition group I, VII or VIII of the Periodic Table are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts which comprise two or more metals supplied to the support, the metal salts or metal salt solutions can be applied simultaneously or in succession.

The supports coated or impregnated with the ruthenium salt solution and/or metal salt solution are subsequently dried, preferably at temperatures from 100 to 150° C., and if desired are calcined at temperatures from 200 to 600° C.

Subsequently, the coated supports are activated by treatment in a stream of gas containing free hydrogen at temperatures from 30 to 600° C., preferably from 150 to 450° C. The stream of gas consists preferably of from 50 to 100% by volume $H_2$ and from 0 to 50% by volume $N_2$.

Where metals from transition group I or VII, in addition to the active metal from transition group VIII, of the Periodic Table are applied in succession to the support, the support can be dried at temperatures from 100 to 150° C. and, if desired, calcined at temperatures from 200 to 600° C. following each application, or impregnation. In this case, the sequence in which the metal salt solutions are applied, or applied by impregnation, is arbitrary.

The metal salt solution is applied to the support or supports in an amount such that from 0.01 to 30% by weight of active metal is present applied to the support, based on the overall weight of the catalyst. This amount is preferably from 0.2 to 15% by weight and, with particular preference, about 0.5% by weight.

The metal surface area on the catalyst 3 is in total from 0.01 to 10 $m^2/g$, more preferably from 0.05 to 5 $m^2/g$ and, in particular, from 0.05 to 3 $m^2/g$ of the catalyst.

The support materials which can be used to prepare the catalysts 3 to be used in accordance with the invention are preferably those which are macroporous and have an average pore diameter of at least 0.1 µm, preferably at least 0.5 µm, and a surface area of not more than 15 $m^2/g$, preferably not more than 10 $m^2/g$, with particular preference for not more than 5 $m^2/g$ and, in particular, not more than 3 $m^2/g$. The average pore diameter of the support preferably lies within a range from 0.1 to 200 µm, in particular from 0.5 to 50 µm.

The surface area of the support is preferably from 0.2 to 15 $m^2/g$, with particular preference from 0.5 to 10 $m^2/g$, in particular from 0.5 to 5 $m^2/g$, and especially from 0.5 to 3 $m^2$ per g of the support.

The surface area of the support is determined in accordance with the BET technique by $N_2$ adsorption, in particular in accordance with DIN 66131. The average pore diameter and pore size distribution are determined by Hg porosimetry, in particular in accordance with DIN 66133. The pore size distribution of the support can preferably be approximately bimodal; the pore diameter distribution having maxima at about 0.6 µm and about 20 µm in the case of the bimodal distribution constitutes a specific embodiment of the invention.

Particular preference is given to a support having a surface area of about 1.75 $m^2/g$ and featuring this bimodal distribution of the pore diameter. The pore volume of this preferred support is preferably about 0.53 ml/g.

Examples of macroporous support materials which can be used are activated carbon, silicon carbide, alumina, silica, titanium dioxide, zirconium dioxide, magnesium oxide, zinc oxide or mixtures thereof. Preference is given to alumina and zirconium oxide.

Further details regarding catalyst 3 and its preparation can be found in DE-A 196 04 791.9, the relevant content of which is incorporated fully into the present specification by reference.

The Process Regime

The hydrogenation carried out in accordance with the invention is conducted at suitable pressures and temperatures. Preference is given in this context to pressures above 10 bar, preferably from approximately 20 to approximately 300 bar. The temperatures employed in the course of the hydrogenation are preferably from approximately 50 to approximately 220° C., more preferably from approximately 80 to approximately 180° C.

The process of the invention can be conducted either continuously or batchwise, preference being given to the continuous process regime.

In the case of the continuous process regime the amount of heterocyclic compound or of the mixture of two or more thereof that is intended for hydrogenation is preferably from approximately 0.05 to approximately 3 kg per liter of catalyst per hour, more preferably from approximately 0.1 to approximately 1 kg per liter of catalyst per hour.

Hydrogenation gases used can be any gases which comprise free hydrogen and do not include harmful quantities of catalyst poisons such as CO, for example. Off-gases from reformers, for example, can be used. It is preferred to use pure hydrogen as the hydrogenation gas.

The hydrogenation of the invention can be conducted in the absence or presence of a solvent or diluent; in other words, it is not necessary to conduct the hydrogenation in solution.

As solvent or diluent it is possible to employ any suitable solvent or diluent. The selection thereof is not critical provided the solvent or diluent employed is able to form a homogeneous solution with the heterocyclic substrate. The solvent or diluent may comprise water, for example.

Examples of suitable solvents or diluents include the following:

straight-chain or cyclic ethers, such as tetrahydrofuran or dioxane, and aliphatic alcohols in which the alkyl radical has preferably 1 to 10 carbon atoms, in particular 3 to 6 carbon atoms.

Examples of alcohol which can be used with preference are isopropanol, n-butanol, isobutanol and n-hexanol.

In the text below, the process of the invention will be elucidated further with reference to the number of working examples.

EXAMPLES

Preparation of Catalyst A

A meso/macroporous alumina support in the form of 3–5 mm beads having a total pore volume of 0.44 $cm^3/g$, with 0.09 $cm^3/g$ (20% of the total pore volume) being formed by pores having a diameter in the range from 50 nm to 10,000 nm and 0.35 $cm^3/g$ (80% of the total pore volume) being formed by pores having a diameter in the range from 2 nm to 50 nm, said support having an average pore diameter of 11 nm and a surface area of 268 $m^2/g$, was impregnated with an aqueous ruthenium(III) nitrate solution. The volume of solution absorbed by the support in the course of impregnation corresponded approximately to the pore volume of the support used. Subsequently, the support impregnated with the ruthenium(III) nitrate solution was dried at 120° C. and activated (reduced) at 200° C. in a stream of hydrogen. The catalyst prepared in this way contains 0.5% by weight of ruthenium, based on the weight of the catalyst. The ruthenium surface area was 0.72 $m^2/g$, and the ratio of ruthenium surface area to support surface area was 0.0027.

Example 1

8 g of catalyst A were placed in a basket insert in a 300 ml pressure reactor. The reactor was subsequently charged with 100 g of pyridine. The hydrogenation was conducted with pure hydrogen at a pressure of from 150 to 250 bar and a temperature of 180° C. Hydrogenation was continued until hydrogen was no longer taken up (0.5 h) and the reactor was then let down. The pyridine conversion was 100%. The yield of piperidine was 99%.

Example 2

8 g of catalyst A were placed in a basket insert in a 300 ml pressure reactor. The reactor was subsequently charged with 40 g of pyridine and 80 ml of THF. The hydrogenation was conducted with pure hydrogen at a pressure of 200 bar and a temperature of 120° C. Hydrogenation was continued until hydrogen was no longer taken up (2 h) and the reactor was then let down. The pyridine conversion was 100%. The yield of piperidine was 98.6%.

Example 3

8 g of catalyst A were placed in a basket insert in a 300 ml pressure reactor. The reactor was subsequently charged with 50 g of pyridine and 80 ml of THF. The hydrogenation was conducted with pure hydrogen at a pressure of from 50 bar and a temperature of 120° C. Hydrogenation was continued until hydrogen was no longer taken up (3 h) and the reactor was then let down. The pyridine conversion was 100%. The yield of piperidine was 98.3%.

Example 4

8 g of catalyst A were placed in a basket insert in a 300 ml pressure reactor. The reactor was subsequently charged with 40 g of pyridine and 80 ml of THF. The hydrogenation was conducted with pure hydrogen at a pressure of from 10 bar and a temperature of 120° C. Hydrogenation was continued until hydrogen was no longer taken up (12 h) and the reactor was then let down. The pyridine conversion was 100%. The yield of piperidine was 98.1%.

Example 5

1.2 l of catalyst A were placed in an electrically heatable through-flow reactor. Subsequently, the hydrogenation of pyridine was commenced, without prior activation, at $2 \times 10^7$ Pa and 160° C. The hydrogenation was performed continuously in the upflow mode, a fraction of the hydrogenation discharge being recycled via a circulation pump and admixed to the starting material upstream of the reactor. Based on the amount of pyridine, ten times the amount of hydrogenation product were thus added as solvent. From 500 to 600 l of $H_2$/h were let off at the top of the separator. The amount of pyridine supplied continuously to the reactor corresponded to a space velocity of 0.3 kg/l×h.

As a function of the reaction temperatures, the product compositions as determined by gas chromatography which resulted under steady state reaction conditions were as follows:

| T/°C. | piperidine/% | pyridine/% | n-pentyl-amine | di-n-pentylamine | others |
|---|---|---|---|---|---|
| 175 | 94.45 | 0 | 0.93 | 0.24 | 4.38 |
| 160 | 98.32 | 0 | 0.29 | 0 | 1.39 |
| 150 | 99.39 | 0 | 0.16 | 0 | 0.45 |
| 120 | 99.86 | 0 | 0.14 | 0 | 0 |

The service life of the catalyst under the selected conditions was at least 1000 h without any observed reduction in activity and selectivity.

We claim:

1. A process for hydrogenating pyridine, an alkylpyridine or a mixture of two or more thereof by contacting pyridine or the alkylpyridine or the mixture of two or more thereof with a hydrogen-containing gas at a temperature in the range of 50 to 120° C. in the presence of a catalyst comprising as active metal ruthenium alone or together with a least one metal from transition group I or VII of the Periodic Table, applied to a support, wherein the support has macropores having an average pore diameter of at least 50 nm.

2. A process as claimed in claim 1, wherein the catalyst comprises as active metal ruthenium alone or together with at least one metal from transition group I or VII of the Periodic Table, applied to a support, the support having an average pore diameter of at least 50 nm and a BET surface area of more than 30 $m^2/g$ and the amount of active metal being from 0.01 to 30% by weight, based on the overall weight of the catalyst.

3. A process as claimed in claim 1, wherein the catalyst comprises as active metal ruthenium alone or together with at least one metal from transition group I or VII of the Periodic Table in an amount of from 0.01 to 30% by weight, based on the overall weight of the catalyst, applied to a support, from 10 to 50% of the pore volume of the support being formed by macropores having a pore diameter in the range from 50 nm to 10,000 nm and from 50 to 90% of the pore volume of the support being formed by mesopores having a pore diameter in the range from 2 to 50 nm, the sum of the pore volumes adding to 100%.

4. A process as claimed in claim 1, wherein the catalyst comprises as active metal ruthenium alone or together with at least one metal from transition group I or VII of the Periodic Table in an amount of from 0.01 to 30% by weight, based on the overall weight of the catalyst, applied to a support, the support having an average pore diameter of at least 0.1 µm and a BET surface area of not more than 15 $m^2/g$.

5. A process as claimed in claim 1, wherein the support comprises activated carbon, silicon carbide, alumina, silica, titanium dioxide, zirconium oxide, magnesium oxide, zinc oxide or a mixture of two or more thereof.

6. A process as claimed in claim 2, wherein the support comprises activated carbon, silicon carbide, alumina, silica, titanium dioxide, zirconium oxide, magnesium oxide, zinc oxide or a mixture of two or more thereof.

7. A process as claimed in claim 3, wherein the support comprises activated carbon, silicon carbide, alumina, silica, titanium dioxide, zirconium oxide, magnesium oxide, zinc oxide or a mixture of two or more thereof.

8. A process as claimed in claim 4, wherein the support comprises activated carbon, silicon carbide, alumina, silica, titanium dioxide, zirconium oxide, magnesium oxide, zinc oxide or a mixture of two or more thereof.

9. A process as claimed in claim 1, wherein the hydrogenation is conducted in the presence of a solvent or diluent.

10. A process as claimed in claim 2, wherein the hydrogenation is conducted in the presence of a solvent or diluent.

11. A process as claimed in claim 3, wherein the hydrogenation is conducted in the presence of a solvent or diluent.

12. A process as claimed in claim 4, wherein the hydrogenation is conducted in the presence of a solvent or diluent.

13. A process as claimed in claim 1, wherein the hydrogenation is conducted continuously.

14. A process as claimed in claim 2, wherein the hydrogenation is conducted continuously.

15. A process as claimed in claim 3, wherein the hydrogenation is conducted continuously.

16. A process as claimed in claim 4, wherein the hydrogenation is conducted continuously.

* * * * *

UNITED STATES PATENT AND TRADEMARK OFFICE
CERTIFICATE OF CORRECTION

PATENT NO. : 6,583,286 B1
DATED : June 24, 2003
INVENTOR(S) : Boettcher et al.

It is certified that error appears in the above-identified patent and that said Letters Patent is hereby corrected as shown below:

Title page,
Item [57], ABSTRACT,
Line 3, "compounder" should be -- compound or --.

Signed and Sealed this

Twelfth Day of August, 2003

JAMES E. ROGAN
*Director of the United States Patent and Trademark Office*